US00PP15889P2

(12) United States Plant Patent
Olesen et al.

(10) Patent No.: US PP15,889 P2
(45) Date of Patent: Jul. 26, 2005

(54) MINIATURE ROSE PLANT NAMED 'POULYV001'

(50) Latin Name: *Rosa hybrida*
Varietal Denomination: POULyv001

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 318 days.

(21) Appl. No.: 10/264,510

(22) Filed: Oct. 4, 2002

(51) Int. Cl.[7] ..... A10H 5/00
(52) U.S. Cl. ..... Plt./118
(58) Field of Search ..... Plt./118

(56) References Cited

U.S. PATENT DOCUMENTS

PP11,232 P * 2/2000 Kordes ..... Plt./116
PP11,242 P * 2/2000 Kordes ..... Plt./116

* cited by examiner

*Primary Examiner*—Bruce R. Campell
*Assistant Examiner*—June Hwu

(57) ABSTRACT

A new miniature rose plant which has abundant, cream-colored flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Classification: Botanical: *Rosa hybrida* 'POULyv001'. Commercial: Miniature.

SUMMARY OF THE INVENTION

The present invention constitutes a new and distinct variety of miniature rose plant which originated from a controlled crossing between 'KORkelvia', described and illustrated in U.S. Plant Pat. No. 11,232 issued on Feb. 22, 2000 and 'POULsiana' described and illustrated in U.S. Plant Pat. No. 11,638, dated Nov. 21, 2000. The two parents were crossed and the resulting seeds were planted in a controlled environment. The new variety is named 'POULvy001'.

The new rose may be distinguished from its seed parent, 'KORkleiva', by the following combination of characteristics:

1. The petal count of 'KORkleiva' is 25 to 30, while that of 'POULyv001' is 30 to 35.
2. Typical bloom diameter of 'KORkleiva' is 45 mm, while that of 'POULyv001' is 100 mm.

The new variety may be distinguished from its pollen parent, 'POULsiana' created by the same inventors, by the following combination of characteristics:

1. The bloom color of 'POULsiana' is yellow, while that of 'POULyv001' is yellow-white.
2. The petal count of 'POULsiana' is 15 to 20, while that of 'POULyv001' is 30 to 35.

The objective of the hybridization of this rose variety for commercial culture was to create a new and distinct variety with unique qualities, such as:

1. Uniform and abundant flowers;
2. Vigorous and compact growth;
3. Year-round flowering under glasshouse conditions;
4. Suitability for production from softwood cuttings in pots;

5. Durable flowers and foliage which make a variety suitable for distribution in the floral industry.

This combination of qualities is not present in previously available commercial cultivars of this type and distinguish 'POULyv001' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULyv001' was selected by the inventors as a single plant from the progeny of the hybridization in April of 1999.

Asexual reproduction of 'POULyv001' by cuttings and traditional budding was first done by L. Pernille and Mogens N. Olesen in their nursery in Fredensborg, Denmark in April, 2000. This initial and other subsequent propagations conducted in controlled environments have demonstrated that the characteristics of 'POULyv001' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULyv001'. Specifically illustrated in SHEET 1:

1. Stem showing opened flower, branching and the attachment of leaves, buds, and peduncles;
2. Flower bud, partially opened bud, and open bloom;
3. Flower petals, detached;
4. Sepals, receptacle, and pedicel;
5. Bare stem exhibiting thorns;
6. Leaves.

DETAILED DESCRIPTION OF THE VARIETY

The following is a description of 'POULyv001', as observed in its growth in a field nursery in Jackson County, Oreg., as three year old plants. Color references are made using The Royal Horticultural Society (London, England) Colour Chart, 1995, except where common terms of color are used.

For a comparison, several physical characteristics of the rose variety 'POULsun', a rose variety from the same inventors decribed and illustrated in U.S. Plant Pat. No. 9,716 and issued on Dec. 3, 1996. are compared to 'POULyv001' in Chart 1.

CHART 1

| | 'POULyv001' | 'POULsun' |
|---|---|---|
| Thorn incidence: | None on stem. | Ordinary. |
| General tonality | White Group 155C. | Yellow Group 13A. |
| Bloom diameter | 100 mm. | 50 to 55 mm. |

Parents: 'KORkleiva'×'POULsiana'.

Flower and flower bud:

Blooming habit: Recurrent.

Flower bud:

*Size.*—Upon opening, 30 mm in length from base of receptacle to end of bud.

*Bud form.*—Globular.

*Bud color.*—As sepals unfold, petal surface is Yellow Group 4C with intonations of Red Group 47B at the margins.

*Sepals.*—Yellow-Green Group 144A. Medium foliaceous appendages on three of the five sepals. Surfaces of sepals are slightly pubescent. Stipitate glands are present in very limited quantities. Shape: Sepal apex is cirrose. Base is flat at union with receptacle. Size: 24 mm long and 10 mm wide.

*Receptacle*—Surface: Smooth Shape: Funnel-shaped. Size: 7 mm (h)×7 mm (w). Color: Yellow-Green Group 144A.

*Peduncle.*—Surface: Scant stipitate glands present. Length: 35 to 40 mm average length. Color: Yellow-Green Group 144 A and B. Strength: Strong.

*Borne.*—1–2 buds per stem.

*Anthocyanin.*—Present on peduncle when grown under high light conditions. Greyed-Purple Group 185D.

Flower bloom:

*Fragrance.*—Light.

*Duration.*—As a pot plant, flowers last from 6 to 8 days. Petals fall cleanly away from plant.

*Size.*—Large for a 10 to 12 cm pot rose. Average flower diameter is 100 mm when open.

*Form.*—Shape of flower when viewed from the side: Upon opening, upper part: Flat. Upon opening, lower part: Flattened convex. Open flower, upper part: Convex. Open flower, lower part: Concave.

*Petalage.*—Double: 30 to 35 petals under normal conditions with 5 to 7 petaloids.

Color:

*Upon opening, petals.*—Outermost petals: Outer Side: Yellow Group 4D. Inner Side: Yellow Group 4D. Innermost petals: Outer Side: Yellow Group 4D. Inner Side: Yellow Group 4D.

*Upon opening, basal petal spots.*—Outer side: Yellow Group 4C. Inner Side: Yellow Group 4C.

*After opening, petals.*—Outermost petals: Outer Side: Yellow Group 4D to White Group 155A. Inner Side: Yellow Group 4D to White Group 155A. Innermost petals: Outer Side: Yellow Group 4D to White Group 155A. Inner Side: Yellow Group 4D to White Group 155A.

*After opening, basal petal spots.*—Outer side: Yellow Group 4C. Inner Side: Yellow Group 4C.

General tonality: On open flower Yellow Group 4D to White Group 155A. No change in the general tonality at the end of the $7^{th}$ day. Afterwards, general tonality is Yellow Group 4D to White Group 155A.

Petals:

*Petal reflex.*—Slight.

*Petal edge.*—Entire.

*Shape.*—Apex: Rounded. Base: Rounded.

*Size.*—32 mm length by 24 mm wide.

*Texture.*—Smooth.

*Petaloids.*—Quantity: 5 to 7. Size: 18 mm long; 15 to 20 mm wide. Color: White Group 155D.

*Thickness.*—Average.

*Arrangement.*—Informal.

Reproductive organs:

*Pistils.*—Length: 8 mm long. Quantity: 20 to 25.

*Pollen.*—Color: Yellow Group 13A. Quantity: Scant.

*Anthers.*—Size: 1.5 mm long. Color: Yellow-Green Group 154C. Quantity: 45.

*Filaments.*—Color: Yellow-Green Group 154D. Length: 5 to 6 mm.

*Stigmas.*—Superior in location to anthers. Color: Greyed-Purple Group 186B.

*Styles.*—Color: Yellow-Green Group 154D.

*Seed formation.*—Hips: None observed.

PLANT

Plant growth: Moderate, compact. When grown as a 10 cm pot plant, the average height of the plant is 25 cm and the average width is 20 to 25 cm.

Stems:

*Color.*—Young wood: Yellow-Green Group 144A. Older wood: Yellow-Green Group 144A.

*Prickles.*—Incidence: 4 on average per 10 cm of stem. Size: 10 mm. Color: Greyed-Red Group 183C. Shape: Linear.

*Surface.*—Young wood: Smooth. Older wood: Smooth.

Plant foliage: Typical number of leaflets on leaves in middle of the stem: 5 leaflets.

*Leaf size.*—85 mm (l)×60 mm (w).

*Quantity.*—Average.

*Color.*—Upper Leaf Surface: Yellow-Green Group 137A. Lower Leaf Surface: Yellow-Green Group 146D.

*Juvenile foliage.*—Upper Leaf Surface: Green Group 144A. Lower Leaf Surface: Green Group 144A.

Plant leaves and leaflets:

*Stipules.*—Size: 4 mm long. Color: Yellow-Green Group 144 A and B. Stipitate glands: Present on edges of stipules.

*Petiole.*—Length: 20 mm. Color: Yellow-Green Group 144A. Underneath: Yellow-Green Group 144A. Margins: Yellow-Green Group 146A.

*Rachis.*—Color: Yellow-Green Group 144A. Underneath: Yellow-Green Group 137A. Margins: Yellow- Green Group 146B. Prickles: 1 to 2 on undersides of rachis.

*Leaflet.*—Edge: Serrated. Surface Texture: Smooth. Shape: Ovate. Apex: Acute. Base: Acute. Glossiness: Somewhat glossy. Thickness: Thick. Arrangement: Odd pinnate. Venation: Reticulate.

Disease resistance: Average resistance to mildew, black spot, and *Botrytis* under normal growing conditions in Jackson County, Oreg.

Cold tolerance: 'POULyv001' has been found cold tolerant to USDA cold hardiness zone 6.

We claim:

1. A new and distinct variety of rose plant of the miniature class, substantially as herein illustrated and described as a distinct and novel rose variety due to its abundant, cream-colored flowers, vigorous growth, compact habit, suitability for production from softwood cuttings in pots, and durable flowers and foliage which make the variety suitable for distribution in the floral industry.

* * * * *

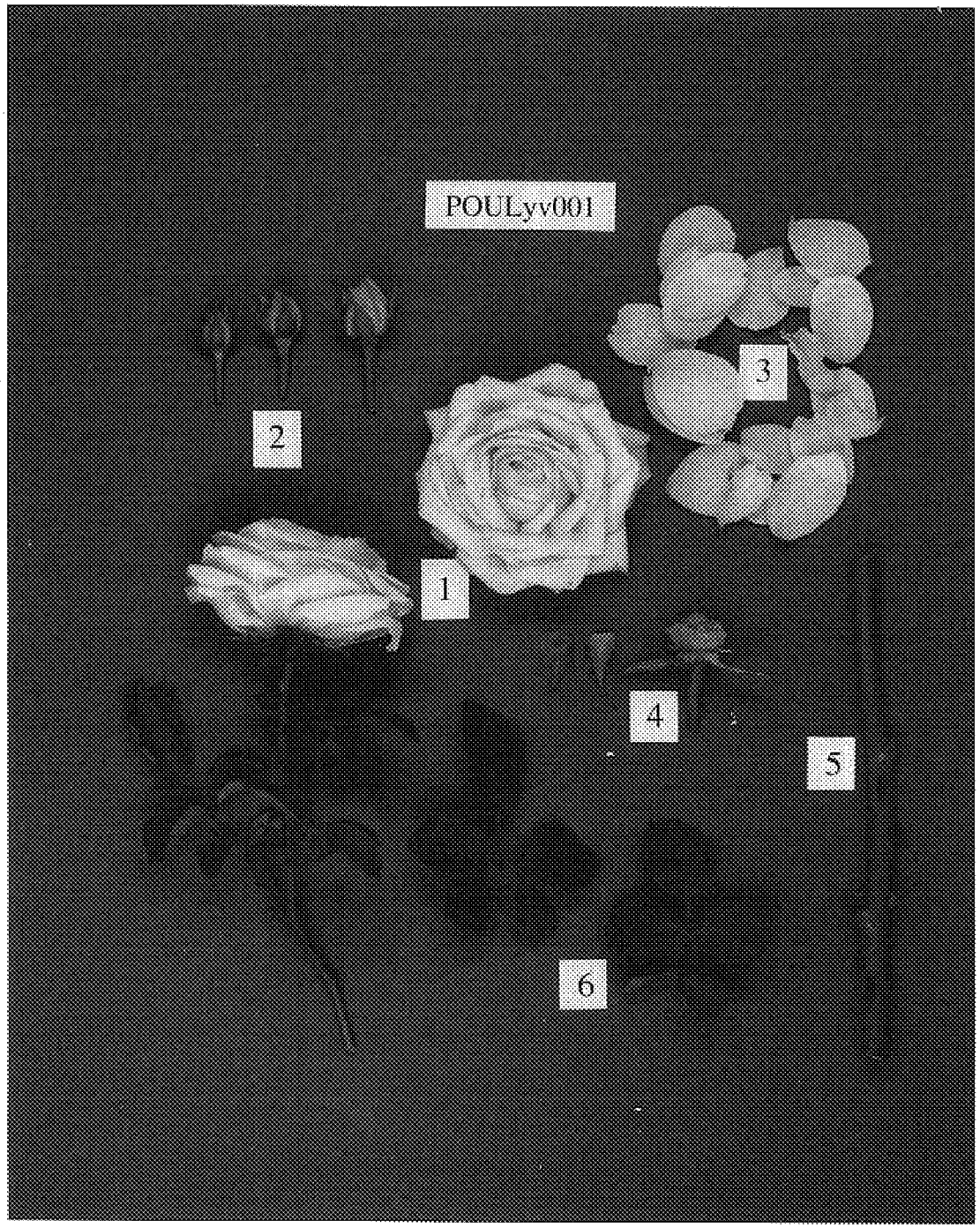
POULyv001
1
2
3
4
5
6